(12) United States Patent
Maekubo et al.

(10) Patent No.: US 12,005,200 B2
(45) Date of Patent: Jun. 11, 2024

(54) CATHETER HANDLE AND CATHETER INCLUDING SAME

(71) Applicant: KANEKA CORPORATION, Osaka (JP)

(72) Inventors: Naotake Maekubo, Okaya (JP); Daichi Kamiyama, Settsu (JP)

(73) Assignee: KANEKA CORPORATION, Osaka (JP)

(*) Notice: Subject to any disclaimer, the term of this patent is extended or adjusted under 35 U.S.C. 154(b) by 828 days.

(21) Appl. No.: 16/965,562

(22) PCT Filed: Oct. 15, 2018

(86) PCT No.: PCT/JP2018/038241
§ 371 (c)(1),
(2) Date: Jul. 28, 2020

(87) PCT Pub. No.: WO2019/150664
PCT Pub. Date: Aug. 8, 2019

(65) Prior Publication Data
US 2021/0046285 A1  Feb. 18, 2021

(30) Foreign Application Priority Data
Jan. 31, 2018  (JP) ................................ 2018-015107

(51) Int. Cl.
*A61M 25/01* (2006.01)
*A61M 25/09* (2006.01)

(52) U.S. Cl.
CPC .... *A61M 25/0136* (2013.01); *A61M 25/0147* (2013.01); *A61M 25/09* (2013.01); *A61M 2205/0233* (2013.01)

(58) Field of Classification Search
CPC .......... A61M 25/0136; A61M 25/0147; A61M 25/09; A61M 2205/0233
See application file for complete search history.

(56) References Cited

U.S. PATENT DOCUMENTS

| | | | |
|---|---|---|---|
| 9,174,024 B1* | 11/2015 | Romoscanu | A61B 34/30 |
| 2012/0130218 A1* | 5/2012 | Kauphusman | A61B 5/6852 |
| | | | 600/585 |
| 2017/0312482 A1* | 11/2017 | Schneider | A61M 25/0147 |

FOREIGN PATENT DOCUMENTS

JP  2013-192670 A  9/2013

OTHER PUBLICATIONS

International Search Report for PCT/JP2018/038241 (PCT/ISA/210) mailed on Jan. 8, 2019.
(Continued)

*Primary Examiner* — Nathan R Price
*Assistant Examiner* — Tania Ismail
(74) *Attorney, Agent, or Firm* — Birch, Stewart, Kolasch & Birch, LLP

(57) ABSTRACT

A catheter handle (1) includes handle body (2), and rotary member (3) being free to rotate with respect to the handle body (2) and connected to the wire. The handle body (2), in a planar view from a rotation axis direction of the rotary member (3), has second space (12) for the conductive wire is located from more distal side to more proximal side than first space (11) for the rotary member (3). The operating part (4) of the rotary member (3) is disposed on one side, and the second space (12) is disposed on another side, in the width direction of the handle (1). Length L1 from the center of the rotation axis to the rotary member (3) on the one side is longer than length L2 from the center of the rotation axis to the rotary member (3) on the another side.

17 Claims, 7 Drawing Sheets

(56) References Cited

OTHER PUBLICATIONS

Written Opinion of the International Searching Authority for PCT/JP2018/038241 (PCT/ISA/237) mailed on Jan. 8, 2019.

* cited by examiner

[Fig. 1]
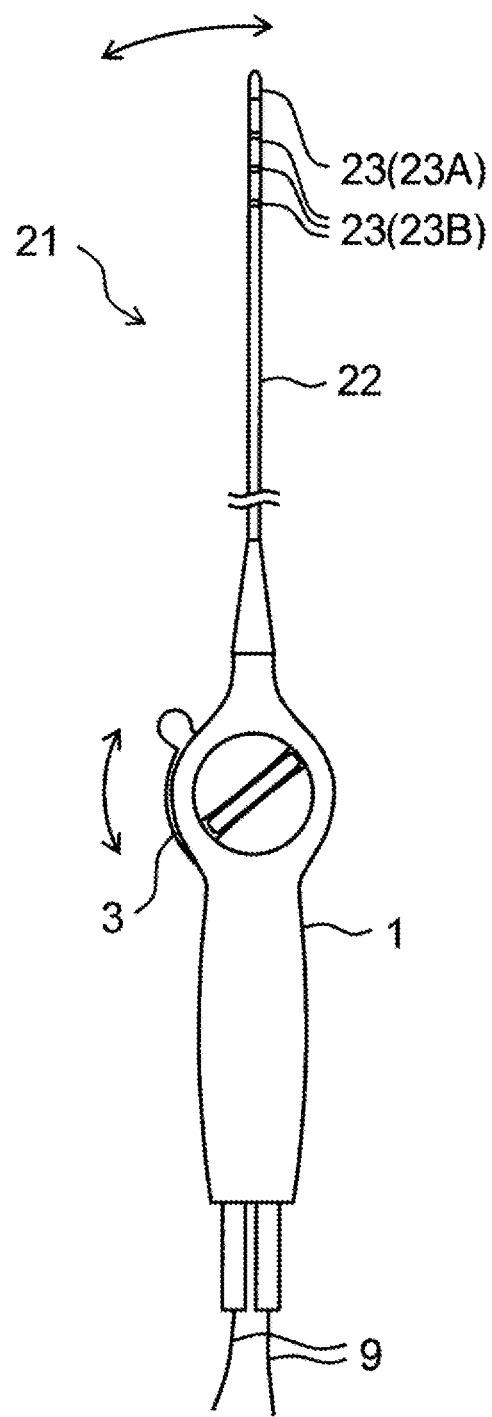

[Fig. 2]
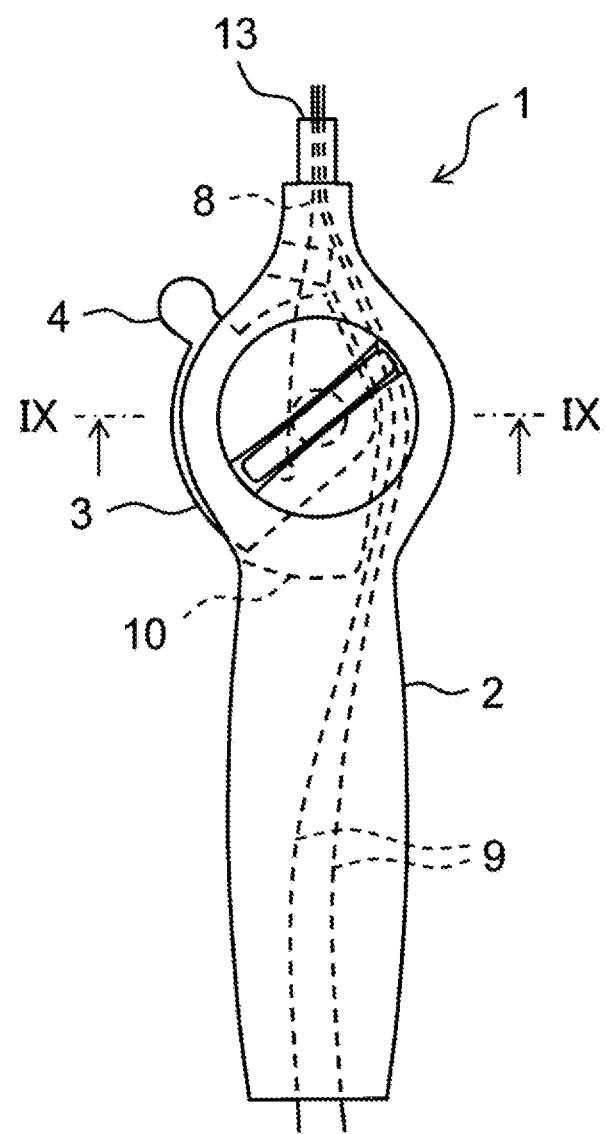

[Fig. 3]
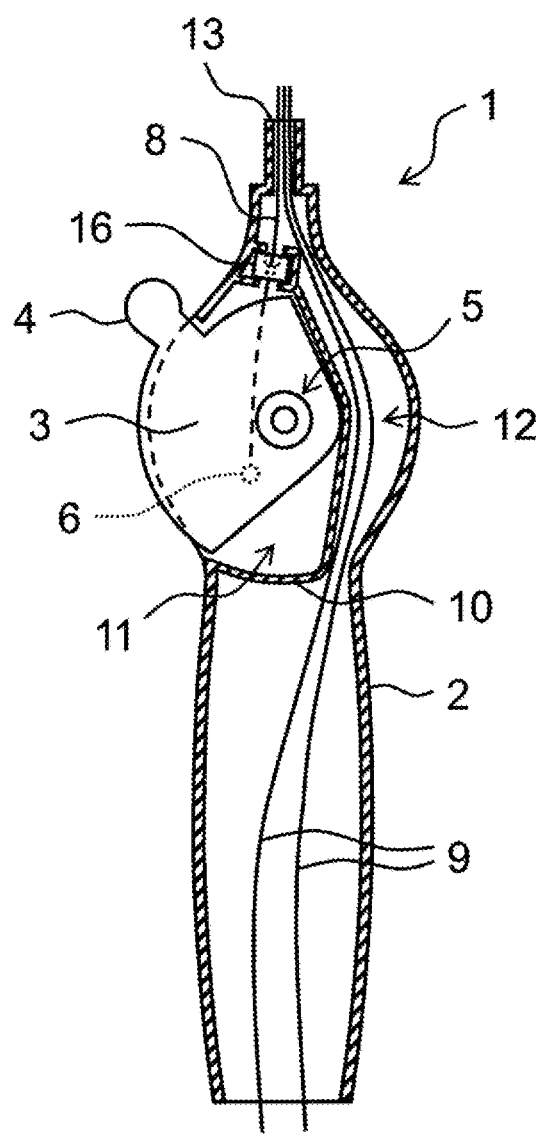

[Fig. 4]
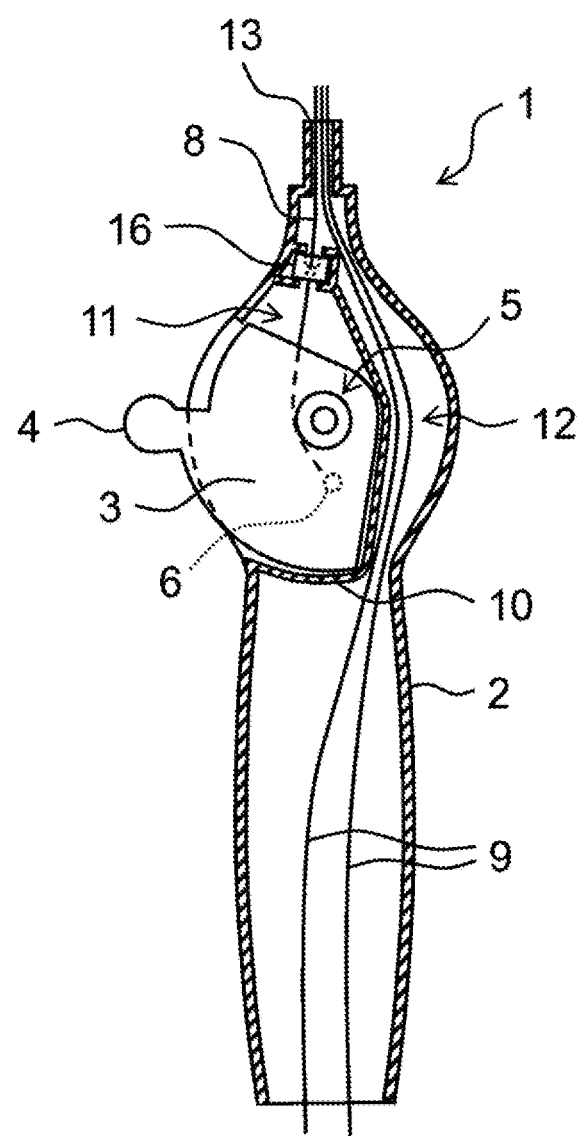

[Fig. 5]
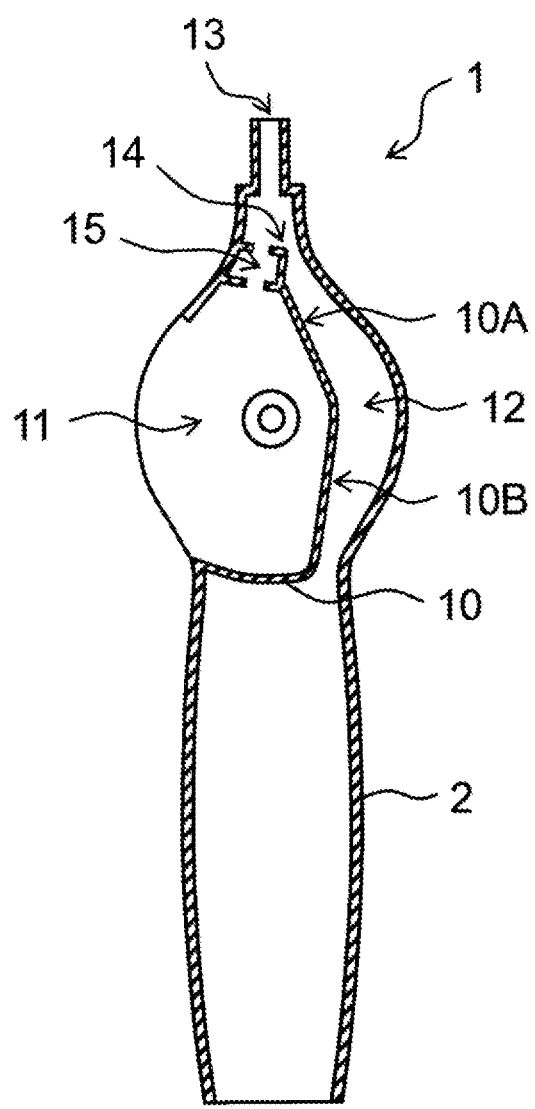

[Fig. 6]
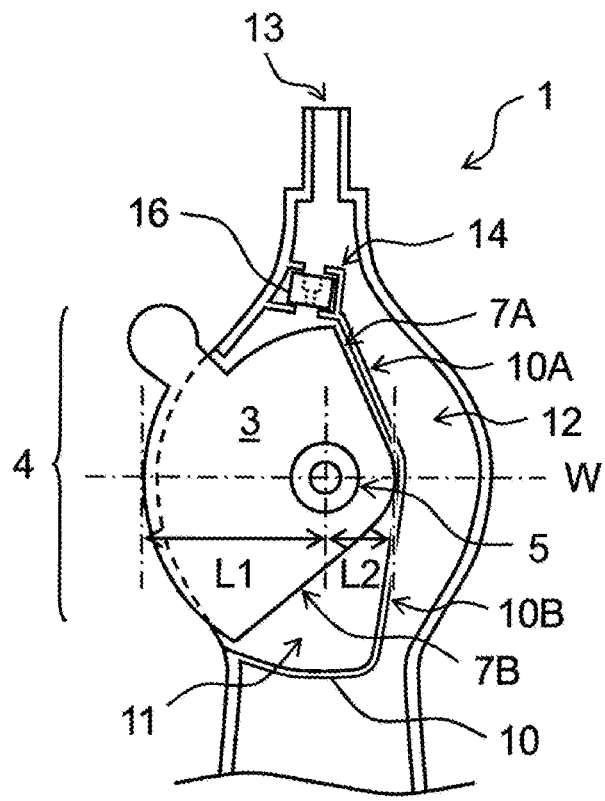
[Fig. 7]
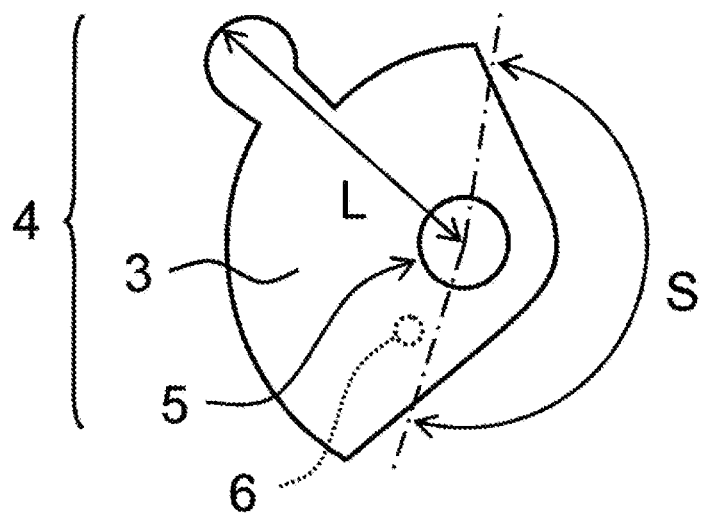

[Fig. 8]
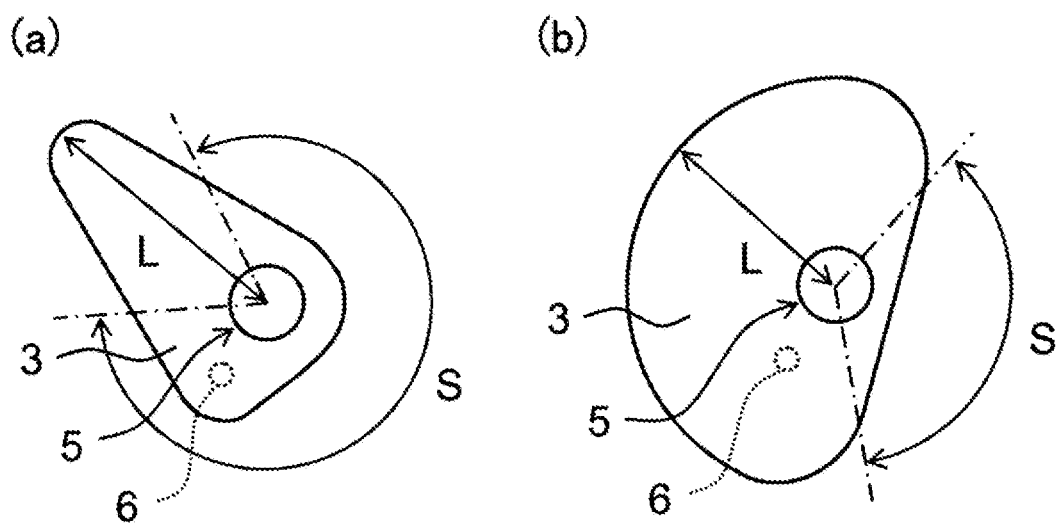
[Fig. 9]
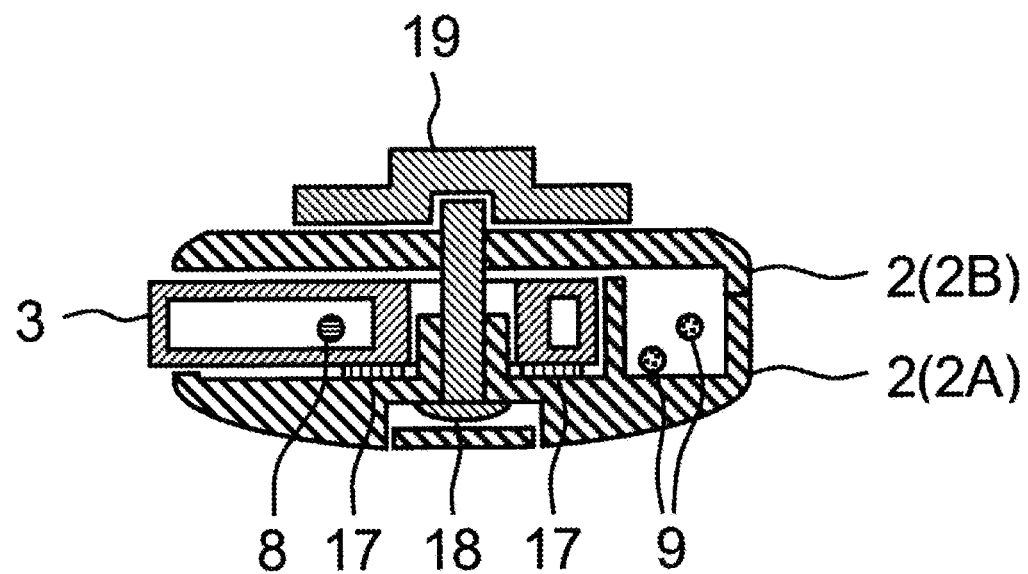

CATHETER HANDLE AND CATHETER INCLUDING SAME

TECHNICAL FIELD

The present invention relates to a catheter handle used for a medical catheter, and a catheter including the same.

BACKGROUND ART

A medical catheter is generally composed of a catheter tube inserted to body lumens such as a blood vessel, a digestive tube, and a urinary duct, and a handle disposed on the proximal side of the catheter tube. A catheter has been known that is configured such that the distal side of the catheter tube can be bent by operating the handle. Such a catheter has, in the catheter tube, wires fixed to the distal side of the catheter tube, and the proximal side of the wire is connected to the handle. The distal side of the catheter tube can be bent by manipulating the handle to pull the wire toward the proximal side or push the wire toward the distal side. An electrode catheter having electrodes on the distal side of the catheter tube further includes conductive wires in the catheter tube, and the proximal side of the conductive wires extends to the inside of the handle. It is noted that "a catheter having electrodes" may be referred to as "an electrode catheter" in the present specification.

In Patent Document 1, for example, a catheter handle is disclosed that allows elongated members such as lead wires of the electrodes and various tubes to be placed inside the catheter handle. The handle has a handle body that is a combination of a first handle member and a second handle member; a rotary operating member that is disposed between the first handle member and the second handle member being free to rotate with respect to the handle body on a rotation axis orthogonal to the longitudinal direction, and that has a rotating plate connected to the base end of an operating wire for bending the tip of the catheter shaft; an adjustment pin that is fixed being unable to rotate with respect to the first handle member, disposed to pierce the rotating plate along the rotation axis of the rotating plate, and that has a male screw on the tip of the adjustment pin; an adjustment grip that is disposed being able to rotate with respect to the second handle member, and has a female screw threadedly engaged with the male screw of the adjustment pin; an elastic member disposed between the handle body and the rotating plate such that operating force of the rotating plate varies in accordance with the depth of threaded engagement of the male screw of the adjustment pin and the female screw of the adjustment grip. The rotary operating member has the rotating plate that is a combination of a first rotary member and a second rotary member formed into a disk shape having the same diameter, and an intermediate member that is disposed between the first rotary member and the second rotary member, and that is fixed being able to rotate with respect to the handle body; the intermediate member is equipped with an introducing path and an external wall formed integrally, and the introducing path allows the elongated members inserted from the tip to the inside of the handle body to extend along the central axis in the longitudinal direction of the handle body, and the external wall of the rotary operating member has a shape according with the shape of the outer perimeter of the rotating plate. The adjustment pin has a through-hole that allows the elongated member extending along the central axis to be inserted (claim 1 of Patent Document 1). The Patent Document 1, which discloses the catheter handle having the handle body and the rotating plate disposed between the first handle member and the second handle member constituting the handle body, also discloses an embodiment in which the elongated member is disposed between the first handle member and the rotating plate in the catheter handle (paragraphs 0003, 0008 of Patent Document 1).

RELATED ART DOCUMENT

Patent Document

Patent Document 1: JP-A-2013-192670

SUMMARY OF THE INVENTION

Problems to be Solved by the Invention

In the catheter handle disclosed in the Patent Document 1, elongated components such as conductive wires are to be disposed on top of the rotating plate in the thickness direction with the result that the handle has a certain thickness. On the other hand, it is desirable for catheter handles to be formed compactly as long as handle operation is not interfered, so that the handle can be placed on any places during treatment with the catheter, and if the handle is placed on the body of a patient the handle is less likely to fall down. In realizing the above situation, the purpose of the present invention is to offer a catheter handle used for an electrode catheter that can be made thin with compact size.

Means for Solving the Problems

The catheter handle of the present invention that can solve the aforementioned problem is a catheter handle connected to a catheter tube to control the catheter tube having a wire and a conductive wire therein, the catheter handle comprising: a handle body connected to a proximal side of the catheter tube; and a rotary member that is disposed being free to rotate with respect to the handle body, and that is connected to a proximal side of the wire; the rotary member having a rotation axis that is orthogonal to both a distal-proximal direction and a width direction of the handle, and having an operating part for rotating the rotary member from outside of the handle body; the handle body, in a planar view from a rotation axis direction of the rotary member, having a first space for rotating the rotary member on the rotation axis and a second space for placing the conductive wire, and the second space extending from more distal side than the first space to more proximal side than the first space; the operating part, on the basis of the rotation axis of the rotary member, disposed on one side in the width direction of the handle, and the second space being disposed on another side in the width direction of the handle; the rotary member having a length L1 that is from the center of the rotation axis to an outer edge of the rotary member on the one side in the width direction is longer than a length L2 that is from the center of the rotation axis to an outer edge of the rotary member on the another side in the width direction, in any condition where the rotary member placed in the first space is rotated on the rotation axis, on an imaginary line that includes a center of the rotation axis and extends in the width direction.

Effects of the Invention

The catheter handle of the present invention can ensure operability of the rotary member connected to the wires, and also can be made thin with compact size.

BRIEF DESCRIPTION OF THE DRAWINGS

FIG. 1 is an overall view of an electrode catheter equipped with a catheter handle.

FIG. 2 is a plan view of the handle provided in the catheter shown in FIG. 1.

FIG. 3 is a plan view of an inner structure of the handle shown in FIG. 2.

FIG. 4 is a plan view of an inner structure of the handle shown in FIG. 2 in a condition where a wire is pulled by a rotary member, FIG. 5 is a plan view of an inner structure of a handle body of the handle shown in FIG. 3 and FIG. 4.

FIG. 6 is a plan view of a handle body and a rotary member showing an inner structure of a major part of the handle shown in FIG. 3.

FIG. 7 is a plan view of a rotary member of the handle shown in FIG. 3.

FIG. 8 is a plan view of another example of a rotary member.

FIG. 9 is a IX-IX cross-sectional view of the handle shown in FIG. 2.

MODE FOR CARRYING OUT THE INVENTION

The present invention relates to a catheter handle used for an electrode catheter, a catheter tube of which has electrodes. The electrode catheter is generally composed of the catheter tube inserted to body lumens such as a blood vessel, and a handle disposed on the proximal side of the catheter tube. The catheter tube has a wire therein, the distal side of which is fixed to the catheter tube and the proximal side of which is fixed to the handle. The distal side of the catheter tube can be bent by operating the handle. The electrode catheter has, in the catheter tube, a conductive wire having the distal side which is connected to the electrode disposed on the distal side of the catheter tube and the proximal side which is connected to a detector or an electric source through the handle to receive an electric signal from the electrode and energize or apply a voltage to the electrode. Such a configuration enables the catheter to measure electrocardiogram and to be used for ablation treatment and defibrillation treatment.

Since the handle for the electrode catheter is provided with the wire and the conductive wire therein, and further with an operating member for operating the wire, which leads to larger number of members placed in the handle, the inner structure of the handle becomes relatively complicated. The catheter handle, which is basically formed around the operating member of the wire (for example, a rotary member), has a problem of interference of the operating member with the conductive wire if the conductive wire is placed in the place where the wire operating member is located. If the conductive wire is tried to be placed in the place where the wire operating member is not located, there is another problem of difficulty in placing the conductive wire due to the limited size of the handle. Furthermore, if the space for placing the conductive wire is small in the handle, the conductive wire is made to be disposed being likely to be under load, which leads to breaking of the conductive wire or damage of insulating coating. On the other hand, larger space for placing the conductive wire results in too larger size of the handle. The catheter handle of the present invention is used for such an electrode catheter, placing operating member for the wire and the conductive wire efficiently to enable the handle to be made thin with compact size.

Hereinafter, the catheter handle and the catheter including the same according to the present invention will be described based on embodiments, however, the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Further, since the dimensions of the various components in the drawings are provided for the purpose of facilitating the understanding of the feature of the present invention, the dimensions may differ from the actual dimensions in some cases.

Firstly, referring to FIG. 1 and FIG. 2, the overall catheter equipped with the catheter handle will be described. Catheter 21 has catheter tube 22 and handle 1 disposed on a proximal side of the catheter tube 22. On a distal side of the catheter tube 22, electrode 23 is provided, and in the catheter tube 22, a wire and a conductive wire are placed. The catheter 21 is, for example, used for examination or treatment of heart arrhythmia by delivering the catheter tube 22 to a patient's heart through blood vessels. In the present invention, the proximal side of the catheter or the catheter handle is the direction of the side of a user's, that is, an operator's hand in the extension direction of the catheter, and the distal side is the opposite direction to the proximal side, that is, the direction of an object of the treatment.

The catheter tube 22 has a flexible annular structure, and may be made of, for example, synthetic resin such as polyolefin resin (such as polyethylene and polypropylene), polyamide resin (such as nylon), polyester resin (such as PET), aromatic polyether ketone resin (such as PEEK), polyetherpolyamide resin, polyurethane resin, polyimide resin, and fluorine resin (such as PTFE, PFA, ETFE); and metals such as stainless steel, carbon steel, and nickel-titanium alloy. The metals may be also used for metal wire embedded in the tube made of synthetic resin. The length in the axial direction (the distal-proximal direction) of the catheter tube 22, which is a few times to several tens of times as long as the catheter handle, is, for example, about 500 mm to 1200 mm. The outer diameter of the catheter tube 22 may be, for example, about 0.6 mm to 3 mm.

The catheter tube 22 has at least one lumen. The catheter tube 22 may have a single lumen structure with one lumen therein, or may have a multi lumen structure with more than one lumen therein. In the lumen of the catheter tube 22, the conductive wire connected to the electrode 23, and the wire for bending the distal side of the catheter tube 22 are placed. The conductive wire may comprise either one conductive wire or a plurality of conductive wires. Since a plurality of the electrodes 23 is generally disposed on the catheter tube 22, the conductive wire also generally comprises the plurality of the conductive wires. The conductive wires may be disposed as a group of the conductive wires. The plurality of the conductive wires may be separately placed in different lumens, or may be placed in the same lumen. Or the plurality of the conductive wires may be bundled to be placed.

On the distal side of the catheter tube 22, the plurality of the electrodes 23 is provided at intervals. In FIG. 1, a tip electrode 23A and a plurality of ring electrodes 23B are disposed. With the electrode catheter, the electrodes 23 are connected with a patient's heart to inspect or treat cardiac dysrhythmia. The electrodes 23 may be made of metal materials such as copper, gold, platinum, aluminum, iron, and an alloy thereof. In order to make the catheter sensitive to radiographic visualization while being used, the electrodes 23 are preferably made of platinum or an alloy thereof.

The catheter handle 1 is disposed on the proximal side of the catheter tube 22. After being assembled as a catheter, the distal side of wire 8 placed in the catheter tube 22 is fixed, for example, to a position at ⅓ from the distal end of the catheter tube 22, and the proximal side of the wire 8 is fixed to the handle 1 (see FIG. 2). The distal side of conductive wire 9 is fixed to the catheter tube 22, specifically to the electrode 23 disposed on the catheter tube 22. The proximal side of the conductive wire 9 is connected to a detector or an electric source through the inside of the handle 1.

As the wire 8, which is disposed to bend the catheter tube 22 by operating the handle 1, a wire may be used that is made of metal such as stainless steel, carbon steel, and nickel-titanium alloy; or synthetic resin such as polyamide resin (such as nylon), polyolefin resin (such as polyethylene and polypropylene), polyester resin (such as PET), aromatic polyether ketone resin (such as PEEK), polyimide resin, and fluorine resin (such as PTFE, PFA, FEP, and ETFE). The wire 8 may comprise either one wire or a structure made of a plurality of wires. The diameter of the wire 8 may be, for example, about 100 µm to 500 µm. The wire 8 may be covered by a coil-like cylindrical body made of metal or synthetic resin.

Conductive wire 9, which just has to include at least a conductive material, may be made of, for example, iron wire, silver wire, stainless wire, copper wire, tungsten wire, nickel titanium wire, or an alloy thereof. The conductive wire 9 preferably include the conductive material as a core material covered by an insulating material. The insulating material may include fluorine resin (such as PTFE, PFA, FEP, and ETFE), polyolefin resin (such as polyethylene and polypropylene), polyvinyl chloride resin, and the like.

Details of the catheter handle will be described referring to FIG. 2 to FIG. 9. It is noted that FIG. 3 shows the condition where the wire is pulled by the rotary member in the least degree, and FIG. 4 shows the condition where the wire is pulled by the rotary member in the fullest degree. In FIG. 6, hatching is omitted in the cross section of the handle body for the sake of convenience.

The handle 1 includes handle body 2 to which the proximal side of the catheter tube 22 is connected, and rotary member 3 that is free to rotate with respect to the handle body 2. The rotary member 3 has a rotation axis 5 orthogonal to both the distal-proximal direction and the width direction of the handle 1, and is configured such that rotation of the rotary member 3 is possible on the rotation axis 5 on the plane including both the distal-proximal direction and the width direction. The rotating of the rotary member 3 means rotation of the rotary member 3 on the rotation axis 5 that is fixed. The rotary member 3 may have a configuration in which transfer of the rotary member 3 itself is possible in the handle 1, as necessary, which is different from the rotating of the rotary member 3.

In the handle 1, the distal-proximal direction is the direction extending from the proximal side to the distal side of the handle 1 described above or the opposite direction, and the width direction is the direction orthogonal to the distal-proximal direction. A rotation axis direction is the direction in which the rotation axis 5 extends. The handle 1 has an upper side and a lower side on the basis of the rotation axis direction, and the rotation axis direction corresponds to a thickness direction of the handle 1. FIG. 2 shows an external view of the handle 1 seeing from the upper side.

In the handle body 2, the wire 8 and the conductive wire 9 are placed along with the rotary member 3. The handle body has a connecting port 13 to be connected to the catheter tube 22 on a distal side, and the proximal side of the wire 8 and the conductive wire 9 placed in the catheter tube 22 extends to the handle body 2 through the connecting port 13. While in FIG. 9, the handle body 2 is disposed so as to sandwich the rotary member 3 from both the upper side and the lower side, the handle body 2 may be disposed on one side of the rotary member 3. In the former case, the handle body 2 may be constituted by, for example, first handle member 2A placed on the lower side of the rotary member 3 and second handle member 2B placed on the upper side of the rotary member 3, and the rotary member 3 is held in an internal space formed by the first handle member 2A and the second handle member 2B. In the latter case, the rotary member 3 is exposed on the surface of the handle body 2. The handle body 2, for example, may be formed from synthetic resin.

The rotary member 3 is disposed being free to rotate with respect to the handle body 2, and connected to a proximal side of the wire 8 as shown in FIG. 3 and FIG. 4. The rotary member 3 is equipped with a wire locking member 6, and the proximal side of the wire 8 is preferably fixed to the wire locking member 6. Means for fixing the wire 8 to the rotary member 3 include, for example, gluing with adhesive, welding with melt synthetic resin, fixing with another parts such as screws, concavo-convex fitting, and a combination thereof. The rotary member 3, for example, may be formed from synthetic resin. The rotary member 3 is preferably configured as a housing in which the proximal side of the wire 8 is placed. In this case, the rotary member 3 is equipped with an insertion port through which the proximal side of the wire 8 can be inserted to the rotary member 3. The housing constituting the rotary member 3 is constituted by two or more members, and the wire 8 may be sandwiched by the members to be fixed.

The handle 1 can make the wire 8 placed in the catheter tube 22 transferred in the distal-proximal direction by rotating the rotary member 3. The handle 1 shown in the figures can make the wire pulled to the proximal side with anti-clockwise rotating of the rotary member 3. Rotating the rotary member 3 from the condition shown in FIG. 3 to the condition shown in FIG. 4 can make the wire 8 pulled to the proximal side to bend the distal side of the catheter tube 22. The angular range in which the rotating of the rotary member 3 is possible is preferably 25° or more, more preferably 35° or more, and preferably 90° or less, more preferably 60° or less, from a viewpoint of good operability of the catheter or the handle. It is noted that the angular range means an angular range in which a point on the rotary member 3 can transfer with the rotating of the rotary member 3 when the point is arbitrary selected.

The handle 1 may make the distal side of the catheter tube 22 bent by pulling the wire 8 to the proximal side, or by pushing the wire 8 to the distal side. With the wire 8 having distal side which is fixed to the distal side of the catheter tube 22, pushing the wire 8 from the proximal side also can make the catheter tube 22 bent.

The rotary member 3 is equipped with an operating part 4 for rotating the rotary member 3 from outside of the handle body 2. The operating part 4 is disposed being exposed on the outside of the handle 1 such that a user can touch the operating part 4 to rotate the rotary member 3. The operating part 4 constitutes a part of the outer edge of the rotary member 3. The operating part 4 includes a projecting portion projecting outward with respect to the rotation axis 5. At least a part of the projecting portion is preferably exposed from the handle body 2. As shown in FIG. 6, the operating part 4 may be formed so as to include a part of an arc whose center is the rotation axis 5 of the rotary member 3. The operating part 4 also may be formed so as to include a projecting portion projecting outward from the arc with respect to the rotation axis 5.

FIG. 5, where an inner structure of the handle body 2 without members such as the rotary member 3 is shown, shows that the handle body 2, in a planar view from the rotation axis direction of the rotary member 3, has a first space 11 for rotating the rotary member 3 and a second space 12 for the conductive wire 9 to be placed are disposed. With the rotating with respect to the rotation axis 5, the rotary member 3 can be rotationally transferred in the first space 11. That is, as shown in FIG. 3 and FIG. 4, before and after the rotating, the position of the rotation axis 5 is not changed and the position of the rotary member 3 in the first place 11 is changed.

The first space 11 is a space where the rotary member is possible to be exist in the handle body 2 before and after the rotating of the rotary member 3, and the rotary member 3 can rotate with respect to the rotation axis 5 in the first space 11. The angular range in which the rotating of the rotary member 3 is possible can be determined in accordance with the size of the first space 11 or the size of an opening for the rotary member 3 disposed on the handle body 2. The angular range in which the rotating of the rotary member 3 is possible may be regulated by a contact of the rotary member 3 with a partition 10 or a projecting portion placed in the handle body or a contact of the operating part 4 with the housing of the handle body 2.

The second space 12 is a space where the conductive wire 9 can be placed in the handle body 2. In FIG. 5, in the handle body 2, a region other than a portion surrounded by the partition 10 and including the first space 11, and other than the undermentioned wire insertion space 15 correspond to the second space 12. The second space 12 extends from more distal side than the first space 11 to more proximal side than the first space 11. With such a configuration, the conductive wire 9 can be inserted from the connecting port 13 to the inside of the handle body 2 to make the proximal side of the conductive wire 9 extend to the rotary member 3 and the proximal side of the first space 11 through the second space 12 in the handle body 2. The narrowest part of the second space 12 preferably has a width of 0.5 mm or more and 3.0 mm or less, more preferably 1.0 mm or more and 2.5 mm or less, which makes the conductive wire 9 stably placed in the second space 12.

As shown in FIG. 6, the handle 1 is disposed such that the operating part 4 is placed on one side in the width direction and the second space 12 is placed on another side in the width direction with respect to the rotation axis 5 of the rotary member 3. The rotary member 3 is configured such that, on an imaginary line W including the center of the rotation axis 5 and extending in the width direction, the rotary member 3 has a length L1 that is from the center of the rotation axis 5 to an outer edge of the rotary member 3 on the one side in the width direction in which the operating part 4 is placed is longer than a length L2 that is from the center of the rotation axis 5 to an outer edge of the rotary member 3 on the another side in the width direction in which the second space 12 is placed. Such a configuration of the handle 1 can make the handle body 2 thin with compact size, and at the same time, can make the second space 12, which enables the conductive wire 9 to be placed without excessive load, formed alongside the first space 11 in the width direction. That is, since the rotary member 3 is formed such that the length L2 that is from the center of the rotation axis to the outer edge is shorter on the another side in the width direction of the handle 1, the second space 12 can be easily kept without increasing the width of the another side in the width direction of the handle body 2. In addition, the conductive wire 9 inserted from the connecting port 13 to the inside of the handle body 2 can be placed in the handle body 2 without bending the conductive wire 9 at a sharp angle. On the other hand, on the one side in the width direction of the handle 1, since the length L1 that is from the center of the rotation axis to the outer edge of the rotary member 3 is formed longer, the operating part 4 can be easily operated with light force. It is noted that the rotary member 3 just has to be placed in the first space 11 and has the aforementioned positional relation in any condition where the rotary member 3 is rotated on the rotation axis 5, and the rotary member 3 preferably has the aforementioned positional relation in an angular range of 60% or more of the angular range in which the rotating of the rotary member 3 is possible, more preferably 75% or more, and even more preferably 90% or more.

Regarding to the above described length L1 and L2 from the center of the rotation axis to the outer edge of the rotary member 3, the length L1 is 1.5 times or more the length L2, more preferably 2.0 times or more, and even more preferably 2.5 times or more. This makes the above described effect easier to be achieved. On the other hand, from the viewpoint of forming the rotary member 3 so as to ensure the strength of the another side in the width direction of the rotary member 3 and so as to be formed with compact size, the length L1 is 8.0 times or less the length L2, more preferably 6.0 times or less, and even more preferably 5.0 times or less.

The shape of the rotary member 3 is not particularly limited as long as the length from the center of the rotation axis to the outer edge of the rotary member 3 is formed longer on the one side of the width direction in which the operating part 4 is placed than on the another side of the width direction that is the side of the second space 12. From the viewpoint of placing the second space 12 for conductive wire 9 in the proximity of the rotation axis 5 of the rotary member 3, the rotary member 3 is preferably formed as described below. As shown in FIG. 7, the rotary member 3 is preferably configured such that based on a maximal length L from the center of the rotation axis to the outer edge of the rotary member, the rotary member 3 has an angle domain where the length from the center of the rotation axis to the outer edge of the rotary member is 0.5L or less, i.e. a minor radius angle domain S, and the angle domain S is a range of a center angle the rotary member 3 has around the rotation axis of 120° or more. The rotary member 3 having such a minor radius angle domain S easily can make the conductive wire 9 placed in the handle body without being bent at a sharp angle. In addition, since the second space 12 can be placed in the proximity of the rotation axis 5, the handle 1 can be made smaller. The minor radius angle domain S is more preferably formed in the range of the center angle the rotary member 3 has around the rotation axis of 150° or more, and even more preferably 180° or more. The maximal length L preferably is a length from the center of the rotation axis to the operating part 4 of the rotary member 3.

FIG. 8 shows another example of the rotary member 3. Both the rotary member 3 shown in FIG. 8 (a), (b) has a shape having the minor radius angle domain S of 120° or more. Even the rotary member 3 having the shape shown in FIG. 8 (a), (b) can keep the second space 12 large to place the conductive wire 9 in the handle body 2, ensuring the operability of the rotary member 3. To form the rotary member 3 as shown in FIG. 8 (*a*), (*b*), the shape of the handle body 2 and the undermentioned partition 10 can be appropriately arranged in accordance with the shape of the rotary member 3.

To pull the wire 8 with lighter force and to finely control the pulling operation, the rotary member 3 is preferably formed such that the length from the center of the rotation axis to the wire locking member 6 is shorter than the length from the center of the rotation axis to the operating part 4. More preferably, the length from the center of the rotation axis to the wire locking member 6 is 80% or less of the length of the operating part 4 from the center of the rotation axis, and even more preferably 65% or less. On the other hand, from the viewpoint of ensuring the length of the wire 8 for pulling by the rotating of the rotary member 3, the length from the center of the rotation axis to the wire locking member 6 is 10% or more of the length from the center of the rotation axis to the operating part 4, and more preferably 20% or more. It is noted that the length from the center of the rotation axis to the wire locking member 6 means the length from the center of the rotation axis of the rotary member 3 to fixing point of the wire locking member 6 to the wire 8. The fixing point of the wire locking member 6 to the wire 8 corresponds to a boundary of a portion where the wire 8 is fixed by the wire locking member 6 and a portion where the wire 8 is not fixed by the wire locking member 6. The wire 8 does not fixed on the distal side of the fixing point. The length from the center of the rotation axis to the operating part 4 means the maximal length of the length from the center of the rotation axis of the rotary member 3 to the operating part 4.

As shown in FIG. 3 and FIG. 4, the wire locking member 6 is preferably located more proximal than the center of the rotation axis of the rotary member 3, which enables the proximal side of the wire 8 to be easily drawn into the handle body 2 by pulling wire 8 when the rotary member 3 is rotated. In this case, the wire locking member 6 is preferably located more proximal than the center of the rotation axis of the rotary member 3 in the angular range of 50% or more in which the rotating of the rotary member 3 is possible, more preferably in the angular range of 70% or more, and even more preferably in the angular range of 90% or more. On the other hand, in the case where the wire is pushed to the side of the catheter tip to bend the catheter, the wire locking member 6 is preferably located more distal than the center of the rotation axis of the rotary member 3. In this case, the wire locking member 6 is preferably located more distal than the center of the rotation axis of the rotary member 3 in the angular range of 50% or more in which the rotating of the rotary member 3 is possible, more preferably in the angular range of 70% or more, and even more preferably in the angular range of 90% or more.

In the case where the catheter has the configuration in which the wire is pulled to bend the tip of the catheter, in the rotary member 3 the wire locking member 6 is preferably configured such that the wire 8 is in contact with the outer perimeter side of the rotation axis 5 of the rotary member 3 in the condition where the wire 8 is pulled to the fullest degree by rotating the rotary member 3. The wire locking member 6 having such a configuration make it easier for the wire 8 to be pulled when the rotary member 3 is rotated. In the condition where the wire 8 is pulled to the least degree by the rotary member 3, that is, where the wire locking member 6 is located on the most distal side with the rotating of the rotary member 3, the wire locking member 6 is preferably located on the one side of the width direction with respect to the center of the rotation axis of the rotary member 3, that is, the side of operating part 4.

From the viewpoint of enabling the wire 8 to be operated with lighter force by rotating the rotary member 3, the center of the rotation axis of the rotary member 3 is preferably located at a place coinciding with the connecting port 13 in the width direction of the handle 1, or located on the another side in the width direction with respect to the connecting port 13. For example, the center of the rotating axis of the rotary member 3 is preferably located at a place coinciding with the connecting port 13 in the width direction of the handle 1, or located at a place on the another side that is 5 mm or less from the connecting port 13 in the width direction, and more preferably 3 mm or less. On the other hand, from the viewpoint of keeping the second space 12 larger, the center of the rotation axis of the rotary member 3 may be located on the one side with respect to the connecting port 13 in the width direction of the handle 1, that is, the side of operating part 4. In this case, from the viewpoint of ensuring operability of the rotary member 3, the center of the rotation axis of the rotary member 3 is preferably located at a place on the one side that is 5 mm or less from the connecting port 13 in the width direction of the handle 1, and more preferably 3 mm or less.

The handle body 2 is preferably formed such that the one side and the another side in the width direction are formed nearly symmetrically. For example, it is preferable that the shape of the another side in the width direction, that is, the side of the second space 12, should not be excessively widened. The handle body 2 is preferably configured, for example, such that, on an imaginary line W including the center of the rotation axis of the rotary member 3 and extending in the width direction, the difference between the length of the one side and the length of the another side on either side of the center of the rotation axis, that is, the difference between the length from the center of the rotation axis to the outer edge of the handle body 2, is preferably 10 mm or less, more preferably 8 mm or less, and even more preferably 5 mm or less.

In the handle body 2, the first space 11 for placing the rotary member 3 and the second space 12 for placing the conductive wire 9 are preferably divided by the partition 10. In other words, the partition 10 is preferably disposed on a boundary between the first space 11 and the second space 12. Such a configuration prevents the conductive wire 9 and the rotary member 3 from being in contact with each other, which makes the conductive wire 9 less likely to be scraped or broken by being entangled into the rotary member 3.

The partition 10 may be disposed on the boundary between the first space 11 and the second space 12 continuously or at intervals. From the viewpoint of preventing the conductive wire 9 and the rotary member 3 from being in contact with each other to the full extent, the partition 10 is preferably disposed on 50% or more of the boundary between the first space 11 and the second space 12, more preferably 70% or more, even more preferably 80% or more, and still more preferably 90% or more. In addition, the partition 10 is preferably disposed on at least a part of the boundary between the first space 11 and the second space 12 where the first space 11 and the second space 12 exist side-by-side. In the case where the partition 10 is disposed at intervals, the length of one interval, that is, a gap length, is preferably 5 mm or less, more preferably 4 mm or less, and even more preferably 3 mm or less from the viewpoint of preventing the conductive wire 9 and the rotary member 3 from being in contact with each other. The lower limit of the length of one interval is not particularly limited, and for example, may be 0.5 mm or more. At least a part of the boundary between the first space 11 and the second space 12 is preferably equipped with a gap or a discontinuous part to draw the wire 8 into the first space 11 and the rotary member 3.

As shown in FIG. 6 and the others, the rotary member 3 is preferably configured such that a part of the outer edge of the rotary member 3 is in contact with a part of the partition 10 by the rotating of the rotary member 3 on the rotation axis 5. The partition 10 having such a configuration can limit the range of the rotating of the rotary member 3 in the handle body 2. In the configuration shown in FIG. 6, the partition 10 is preferably disposed so as to be in contact with a part of the outer edge of the rotary member 3 with clockwise rotating of the rotary member 3, and to be in contact with another part of the outer edge of the rotary member 3 with anticlockwise rotating of the rotary member 3.

In addition, the rotary member 3 and the partition 10 are preferably configured as follows. As shown in FIG. 6, the partition 10 preferably has a first partition straight portion 10A and a second partition straight portion 10B, and the outer edge of the rotary member 3 has a first edge straight portion 7A and a second edge straight portion 7B. By the rotating of the rotary member 3 on the rotation axis 5, the first edge straight portion 7A preferably gets close to the first partition straight portion 10A and the second edge straight portion 7B gets away from the second partition straight portion 10B, or the second edge straight portion 7B gets close to the second partition straight portion 10B and the first edge straight portion 7A gets away from the first partition straight portion 10A. In this case, the first edge straight portion 7A and the first partition straight portion 10A are preferably nearly parallel to each other in the condition of getting close to each other, and the second edge straight portion 7B and the second partition straight portion 10B are preferably nearly parallel to each other in the condition of getting close to each other. It is noted that the condition where the first edge straight portion 7A and the first partition straight portion 10A get close to each other means, as shown in FIG. 6, a condition after the rotary member 3 is clockwise rotated. Such a configuration of the rotary member 3 and the partition 10 can make it easy for the first partition straight portion 10A and the second partition straight portion 10B to surely limit the range of the rotating of the rotary member 3.

As shown in FIG. 5 and FIG. 6, the handle body 2 preferably has a bifurcation part 14 on a distal side of the rotary member 3 to bifurcate the wire 8 and the conductive wire 9 inserted from the distal side (connecting port 13) of the handle body 2, and the bifurcation part 14 has a wire insertion space 15 communicated with the first space 11 is disposed at the bifurcation part 14 in the handle body 2. The bifurcation part 14 is located more distal than the first space 11 in the handle body 2, which bifurcate into a space for placing the wire 8 and a space for placing the conductive wire 9, and the space for placing the wire 8 is to be the wire insertion space 15 and the space for placing the conductive wire 9 is to be the second space 12. The bifurcation part 14 having such a configuration can prevent the conductive wire 9 along with the wire 8 from being drawn into the rotary member 3 and prevent the wire 8 and the conductive wire 9 from scraping each other when the rotary member 3 is rotated to pull the wire 8 to the proximal side or push the wire 8 to the distal side, which prevents the wire 8 from being damaged and bearing excessive load.

The wire insertion space 15 is preferably equipped with a wire guide part 16 having an opening to pass through the wire 8. By inserting the wire 8 into the rotary member 3 through the opening of the wire guide part 16, the wire 8 can be easily drawn to the rotary member 3 to be pulled to the proximal side when the rotary member 3 is rotated. In addition, the wire guide part 16 can prevent the conductive wire 9 from being drawn to the wire insertion space 15 and the rotary member 3. The wire guide part 16 can be made of, for example, synthetic resin.

The opening of the wire guide part 16 preferably has a larger diameter on a distal side of the opening than a diameter on a proximal side of the opening. The wire guide part 16 having such a configuration can make it easier for the wire 8 inserted from the connecting port 13 of the handle body 2 to be inserted to the opening of the wire guide part 16 without excessive load. In the case where the wire 8 is covered by a cylindrical body made of coil-like metal or synthetic resin, the opening of the wire guide part 16 can prevent the cylindrical body from being drawn to the proximal side such that only the wire 8 is introduced to the rotary member 3.

The rotary member 3 is configured to be able to rotate on the rotation axis 5, and at the same time, the rotary member 3 is preferably configured to be able to be positionally fixed to the handle body 2 at an arbitrary rotational angle. The positional fixing can keep the bent shape of the distal side of the catheter tube 22 stable. For the purpose, the handle 1, as shown in FIG. 9, preferably has elastic member 17 between the rotary member 3 and the handle body 2, and the elastic member 17 and the rotary member 3 is preferably in contact with each other. In addition, the rotary member 3 may be configured to be possible to be pressed against the handle body 2 in the rotation axis direction through the elastic member 17. In this case, in a cross-sectional view of the handle 1 along the rotation axis direction, the elastic member 17 is placed between the rotary member 3 and the handle body 2. The rotary member 3 is pressed against the handle body 2 through the elastic member 17, and as a result, the rotary member 3 and the handle body 2 are firmly pressed against the elastic member 17 to prevent the rotary member 3 from freely rotating with respect to the handle body 2. Consequently, since the position of the wire 8 is fixed by fixing the rotational position of the rotary member 3, the bent shape of the distal side of the catheter tube 22 can be fixed, and the electrode 23 of the catheter tube 22 can be stably in contact with an inner wall of a patient's heart and the like. On the other hand, by releasing the press of the rotary member 3 against the handle body 2, the rotary member 3 becomes free to rotate with respect to the handle body 2.

For the elastic member 17, a sheet-like elastic member just has to be disposed between the handle body 2 and the rotary member 3. The elastic member 17 may be disposed between the rotary member 3 and the first handle member 2A or between the rotary member 3 and the second handle member 2B. The shape of the elastic member 17 is not particularly limited. In FIG. 9, the elastic member 17 having an annular shape is disposed so as to surround the rotation axis 5 of the rotary member 3. The elastic member 17 may be attached to the handle body 2 or attached to the rotary member 3. The elastic member 17 is preferably composed of an elastically deformable material including rubber such as silicone rubber, nitrile rubber, fluorine-containing rubber, and natural rubber; styrene-based elastomer such as styrene-isoprene-styrene block copolymer (SIS), styrene-butadiene-styrene block copolymer (SBS), styrene-ethylene-butadiene-styrene block copolymer (SEBS), and styrene-ethylenepropylene-styrene block copolymer (SEPS); and urethane-based elastomer such as polyurethane.

Means for pressing the rotary member 3 against the handle body 2 through the elastic member 17 is not particularly limited, and in FIG. 9, bolt 18 and nut 19 are used. Specifically, at the rotation axis of the rotary member 3 the bolt 18 is placed that pierces the handle body 2 and the rotary member 3, and the nut 19 having a knob and the bolt 18 is screwed together. By screwing up the nut 19 against the bolt 18, the rotary member 3 can be pressed against the handle body 2 through the elastic member 17.

The above described catheter handle of the present invention will be briefly summarized. The catheter handle of the present invention, which is connected to a catheter tube to control the catheter tube having a wire and a conductive wire therein, is characterized by that the catheter handle has a handle body connected to a proximal side of the catheter tube; and a rotary member that is disposed being free to rotate with respect to the handle body and is connected to a proximal side of the wire; the rotary member having a rotation axis that is orthogonal to both a distal-proximal direction and a width direction of the handle, and having an operating part for rotating the rotary member from outside of the handle body; the handle body, in a planar view from a rotation axis direction of the rotary member, having a first space for rotating of the rotary member on the rotary axis and a second space for placing the conductive wire, and the second space extending from more distal side than the first space to more proximal side than the first space; the operating part, on the basis of the rotation axis of the rotary member, being disposed on one side in the width direction of the handle, and the second space being disposed on another side in the width direction of the handle; the rotary member having a length L1 that is from the center of the rotation axis to an outer edge of the rotary member on the one side in the width direction is longer than a length L2 that is from the center of the rotation axis to an outer edge of the rotary member on the another side in the width direction, in any condition where the rotary member placed in the first space is rotated on the rotation axis, on an imaginary line that includes a center of the rotation axis and extends in the width direction.

The catheter handle of the present invention having the above configuration can make the handle body thin with compact size, and at the same time enables the second space for placing the conductive wire to be formed without excessive load on the conductive wire. As for the rotary member pulling the wire, since the length from the center of the rotation axis to the outer edge is made longer on the side of the operating part, the rotary member can be operated with light force. Accordingly, the catheter handle of the present invention can ensure operability of the rotary member, and also can be made thin with compact size.

The handle body preferably has a connecting port on a distal side of the catheter handle to be connected to the catheter tube, wherein the center of the rotation axis is located at a place coinciding with the connecting port in the width direction of the handle, or located on the another side in the width direction with respect to the connecting port. The catheter handle is configured so as to pull the wire to the proximal side by rotating the rotary member, and the center of the rotation axis of the rotary member located in such a position enables the wire to be pulled with lighter force.

The rotary member preferably has a wire locking member fixing the proximal side of the wire, wherein a length from the center of the rotation axis to the wire locking member is shorter than a length from the center of the rotation axis to the operating part. The wire locking member having such a configuration enables the wire to be pulled with lighter force and also can make finely controlled pulling operation easier.

The wire locking member is preferably located on more proximal side than the center of the rotation axis of the rotary member. Such a configuration makes it easier for the wire to be pulled to the proximal side to be drawn into the handle body.

Base on a maximal length L from the center of the rotation axis to an outer edge of the rotary member, the rotary member preferably has an angle domain where a length from the center of the rotation axis to an outer edge of the rotary member is 0.5L or less, and the angle domain is a range of a center angle of 120° or more the rotary member has around the rotation axis. The rotary member made to have such a configuration enables the second space for placing the conductive wire to be in the proximity of the rotation axis of the rotary member, The partition is preferably disposed on a boundary between the first space and the second space. The partition can prevent the conductive wire and the rotary member form being in contact with each other, which makes the conductive wire less likely to be scraped or broken by being entangled into the rotary member.

The rotary member is preferably configured such that a part of the outer edge of the rotary member is in contact with a part of the partition by rotating of the rotary member on the rotation axis. The partition having such a configuration can limit the range of the rotating of the rotary member.

The partition preferably has a first partition straight portion and a second partition straight portion, and the outer edge of the rotary member has a first edge straight portion and a second edge straight portion, and when the rotary member rotates on the rotation axis, the first edge straight portion gets close to the first partition straight portion and the second edge straight portion gets away from the second partition straight portion, or the second edge straight portion gets close to the second partition straight portion and the first edge straight portion gets away from the first partition straight portion. The rotary member and the partition having such a configuration can make it easy for the first partition straight portion and the second partition straight portion to surely limit the range of the rotating of the rotary member.

An elastic member is preferably disposed between the rotary member and the handle body, and the rotary member is possible to be pressed against the handle body in the rotation axis direction through the elastic member. The handle having such a configuration enables the rotary member to be positionally fixed to the handle body at an arbitrary rotational angle by pressing the rotary member against the handle body through the elastic member. Thus, the bent shape of the distal side of the catheter tube can be fixed.

The handle body preferably has the bifurcation part on the distal side of the rotary member to bifurcate the wire and the conductive wire inserted from the distal side of the handle body, and the bifurcation part has a wire insertion space communicated with the first space is disposed at the bifurcation part in the handle body. The bifurcation part having such a configuration in the handle body can prevent the conductive wire along with the wire from being drawn into the rotary member, which prevents the wire from being damaged and bearing excessive load when the rotary member is rotated to pull the wire to the proximal side.

The wire insertion space is preferably equipped with a wire guide part having an opening to pass through the wire, and the opening of the wire guide part has a larger diameter on the distal side of the opening than a diameter on the proximal side of the opening. By passing through the wire into the rotary member through the opening of the wire guide part, the wire can be stably drawn to the rotary member when the rotary member is rotated.

The present invention also provides a catheter having the catheter handle of the present invention, a catheter tube connected to the distal side of the handle body, a wire having a distal side which is fixed to the catheter tube and a proximal side which is fixed to the rotary member, a conductive wire having a distal side which is fixed to the catheter tube and a proximal side which extends through the second space to the proximal side of the rotary member. Since the catheter of the present invention has the aforementioned handle, operability of the handle can be ensured, and also the handle can be made thin with compact size.

The present application claims priority based on Japanese Patent Application No. 2018-015107 filed on Jan. 31, 2018. All the contents described in Japanese Patent Application No. 2018-015107 filed on Jan. 31, 2018 are incorporated herein by reference.

DESCRIPTION OF REFERENCE SIGNS

1: catheter handle
2: handle body, 2A: first handle member, 2B: second handle member
3: rotary member
4: operating part
5: rotation axis
6: wire locking member
7A: first edge straight portion, 7B: second edge straight portion
8: wire
9: conductive wire
10: partition, 10A: first partition straight portion, 10B: second partition straight portion
11: first space
12: second space
13: connecting port
14: bifurcation part
15: wire insertion space
16: wire guide part
17: elastic member
18: bolt
19: knob (nut)
21: catheter
22: catheter tube
23, 23A, 23B: electrode

The invention claimed is:

1. A combination of a catheter handle and a catheter tube to control a catheter tube having a wire and a conductive wire therein, the catheter handle comprising:
a handle body connected to a proximal side of the catheter tube, the handle body having a partition disposed in the handle body; and
a rotary member that is disposed in the handle body so that the rotary member is free to rotate with respect to the handle body, and that is to be connected to a proximal side of the wire, wherein
the rotary member has a rotation axis that is orthogonal to both a distal-proximal direction extending from a distal side to a proximal side of the handle body and a width direction of the handle, an operating part for rotating the rotary member from outside of the handle body,
the handle body has an opening in a side wall, and the rotary member is disposed in the handle body so that the operating part of the rotary member penetrates to the outside of the handle body through the opening of the side wall,
the partition is disposed in the handle body, so that the handle body, in a planar view from a rotation axis direction of the rotary member, has a first space for accommodating the rotary member rotatable on the rotation axis, the first space having the opening in the side wall and being defined by a surface of the partition facing to the opening, and a second space for placing the conductive wire, and the second space continuously extending, around the first space, from the distal side to the proximal side of the handle body inside the handle body, the second space being defined by an inner wall of the handle body and the other surface of the partition opposite to the surface of the partition facing to the opening, the first space and the second space being separated by the partition, and
the rotary member is disposed in the first space of the handle body so that i) the rotary member is regulated to be rotatable around the rotation axis within the first space, ii) a length L1 that is from the center of the rotation axis to an outer edge of the rotary member on a side facing to the opening in the width direction is longer than a length L2 that is from the center of the rotation axis to an outer edge of the rotary member on the other side in the width direction facing to the surface of the partition defining the first space, on an imaginary line that includes a center of the rotation axis and extends in the width direction, and iii) the operating part of the rotary member is rotatable together with the rotary member and with respect to the rotation axis within the opening.

2. The combination of catheter handle and a catheter tube according to claim 1, wherein the handle body comprises a connecting port on a distal side of the catheter handle to be connected to the catheter tube, wherein
the center of the rotation axis is located at a place coinciding with the connecting port in the width direction of the handle, or located on the another side in the width direction with respect to the connecting port.

3. The combination of catheter handle and a catheter tube according to claim 1, wherein
the rotary member has a wire locking member for fixing the proximal side of the wire, and
a length from the center of the rotation axis to the wire locking member is shorter than a length from the center of the rotation axis to the operating part.

4. The combination of catheter handle and a catheter tube according to claim 3, wherein
the rotary member is disposed in the handle body such that the wire locking member is located away from the distal side of the handle body than the center of the rotation axis of the rotary member.

5. The combination of catheter handle and a catheter tube according to claim 1, wherein
based on a maximal length L from the center of the rotation axis to an outer edge of the rotary member,
the rotary member has a narrower portion where a length from the center of the rotation axis to an outer edge of the rotary member is 0.5 L or less, and the narrower portion extends in a range of a center angle of 120° or more around the rotation axis.

6. The combination of catheter handle and a catheter tube according to claim 1, wherein a part of the outer edge of the rotary member is in contact with a part of the partition by rotating of the rotary member on the rotation axis.

7. The combination of catheter handle and a catheter tube according to claim 1, wherein
the partition has a first partition straight portion and a second partition straight portion,
the outer edge of the rotary member has a first edge straight portion and a second edge straight portion,
when the rotary member rotates on the rotation axis, the first edge straight portion gets close to the first partition straight portion and the second edge straight portion gets away from the second partition straight portion, or the second edge straight portion gets close to the second partition straight portion and the first edge straight portion gets away from the first partition straight portion.

8. The combination of catheter handle and a catheter tube according to claim 1, further comprising an elastic member between the rotary member and the handle body, wherein
the rotary member is possible to be pressed against the handle body in the rotation axis direction through the elastic member.

9. The combination of catheter handle and a catheter tube according to claim 1, wherein
the handle body has a bifurcation part on a distal side of the rotary member to bifurcate the wire and the conductive wire to be inserted from the distal side of the handle body, and
the bifurcation part has a wire insertion space communicated with the first space in the handle body.

10. The combination of catheter handle and a catheter tube according to claim 9, wherein
the wire insertion space has a wire guide part having an opening to pass through the wire,
the opening of the wire guide part has a larger diameter on a distal side of the opening than a diameter on a proximal side of the opening.

11. A catheter, comprising:
the catheter handle according to claim 1;
a catheter tube connected to the distal side of the handle body;
a wire having a distal side which is fixed to the catheter tube and a proximal side which is fixed to the rotary member; and
a conductive wire having a distal side which is fixed to the catheter tube and a proximal side which extends through the second space to the proximal side of the rotary member, wherein the wire and the conductive wire are disposed in the catheter tube.

12. A catheter handle to control a catheter tube having a wire and a conductive wire therein, the catheter handle comprising:
a handle body to be connected to a proximal side of the catheter tube, the handle body having a partition disposed in the handle body; and
a rotary member that is disposed in the handle body so that the rotary member is free to rotate with respect to the handle body, and that is to be connected to a proximal side of the wire, wherein
the rotary member has a rotation axis that is orthogonal to both a distal-proximal direction extending from a distal side to a proximal side of the handle body and a width direction of the handle, an operating part for rotating the rotary member from outside of the handle body, the handle body has an opening in a side wall, and the rotary member is disposed in the handle body so that the operating part of the rotary member penetrates to the outside of the handle body through the opening of the side wall,
the partition is disposed in the handle body, so that the handle body, in a planar view from a rotation axis direction of the rotary member, has a first space for accommodating the rotary member rotatable on the rotation axis, the first space having the opening in the side wall and being defined by a surface of the partition facing to the opening, and a second space for placing the conductive wire, and the second space continuously extending, around the first space, from the distal side to the proximal side of the handle body inside the handle body, the second space being defined by an inner wall of the handle body and the other surface of the partition opposite to the surface of the partition facing to the opening, the first space and the second space being separated by the partition, and
the rotary member is disposed in the first space of the handle body so that i) the rotary member is regulated to be rotatable around the rotation axis within the first space, ii) a length L1 that is from the center of the rotation axis to an outer edge of the rotary member on a side facing to the opening in the width direction is longer than a length L2 that is from the center of the rotation axis to an outer edge of the rotary member on the other side in the width direction facing to the surface of the partition defining the first space, on an imaginary line that includes a center of the rotation axis and extends in the width direction, and iii) the operating part of the rotary member is rotatable together with the rotary member and with respect to the rotation axis within the opening.

13. The combination of catheter handle and a catheter tube according to claim 1, wherein the second space is formed alongside the first space in the width direction.

14. The combination of catheter handle and a catheter tube according to claim 1, wherein the rotary member is rotatably disposed in the first space of the handle body so that with respect to a longitudinal axis passing through the center of the rotation axis of the rotary member, the length L1 on the one side of the width direction in an entire area of the one side is longer than the length L2 on the other side of the width direction in an entire area of the other side.

15. The combination of catheter handle and a catheter tube according to claim 1, wherein the operating part constitutes a part of the outer edge of the rotary member.

16. The combination of catheter handle and a catheter tube according to claim 1, wherein the second space extends from a distal end to a proximal end, around the first space accommodating the rotary member, in the distal-proximal direction, and the rotary member does not exist in the second space.

17. The combination of catheter handle and a catheter tube according to claim 1, wherein the rotary member and the wire are configured so that when the rotary member is rotated, the wire is in contact with an outer perimeter side of the rotation axis of the rotary member.

* * * * *